United States Patent [19]

Takahata et al.

[11] 4,351,958

[45] Sep. 28, 1982

[54] PROCESS FOR PRODUCING ORTHOALKYLATED AROMATIC AMINE

[75] Inventors: Kazunori Takahata, Otake; Katsuo Taniguchi, Iwakuni, both of Japan

[73] Assignee: Mitsui Petrochemical Industries, Ltd., Tokyo, Japan

[21] Appl. No.: 297,166

[22] Filed: Aug. 28, 1981

[51] Int. Cl.$^3$ ............................................. C07C 85/24
[52] U.S. Cl. .................................... 564/409; 564/437
[58] Field of Search ....................................... 564/409

[56] References Cited

U.S. PATENT DOCUMENTS

| | | | |
|---|---|---|---|
| 2,814,646 | 11/1957 | Kolka et al. | 260/577 |
| 2,831,898 | 4/1958 | Ecke et al. | 564/409 X |
| 3,123,644 | 3/1964 | Olin | 564/409 |
| 3,275,690 | 9/1966 | Stroh et al. | 564/409 |
| 3,654,331 | 4/1972 | Klopfer | 260/448 |
| 3,674,852 | 7/1972 | Averill et al. | 564/409 |

FOREIGN PATENT DOCUMENTS

| | | | |
|---|---|---|---|
| 384569 | 8/1955 | Japan | 564/409 |
| 49-29177 | 8/1974 | Japan | 564/409 |
| 50-137934 | 11/1975 | Japan | 564/407 |

OTHER PUBLICATIONS

Albright et al., "I/EC–Unit Processes Review," vol. 52, No. 6, pp. 533–542 (Jun. 1960).
Friedel Crafts and Related Reactions, vol. 2, Part 1, pp. 576–577, by G. A. Olah, Published by Interscience Publishers (1964).
Industrial and Engineering Chemistry, vol. 43, No. 7, pp. 1579–1583 (1951).

*Primary Examiner*—John Doll
*Attorney, Agent, or Firm*—Armstrong, Nikaido, Marmelstein & Kubovcik

[57] ABSTRACT

An orthoalkylated aromatic amine is produced at a high selectivity from the reaction of an aromatic amine having at least one hydrogen atom at the ortho-positions and a primary or secondary alcohol under heating in the presence of a catalyst containing, as a main constituent, iron oxides.

7 Claims, No Drawings

PROCESS FOR PRODUCING ORTHOALKYLATED AROMATIC AMINE

The present invention relates to a process for selectively producing orthoalkylated aromatic amine at a high yield and, more specifically, it relates to a process for producing an orthoalkylated aromatic amine from an aromatic amine having at least one hydrogen atom at the ortho-positions and a primary or secondary alcohol under heating in the presence of a catalyst containing, as a main constituent, iron oxides.

The orthoalkylated aromatic amines are useful, as intermediates for producing pharmaceutical preparations, pesticides, dyes, resin stabilizers, rubber compounding ingredients and the like.

It has been known heretofore in the art, as a process for producing alkylated aromatic amines such as o-toluidine, 2,6-dimethylaniline and the like, that corresponding alkylated phenols such as o-cresol, 2,6-xylenol and the like are reacted with ammonia or amines under heating in the presence of a dehydration catalyst such as alumina, silica alumina or the like. However, there are problems in this reaction of the phenols having an alkyl group at the ortho-positions with ammonia or amines that the reaction rate is remarkably slow, as compared with the reaction of phenol with ammonia or amines and that the selectivity thereto and the yield thereof are low. Furthermore, since the decrease in the activity of the above-mentioned catalyst is remarkable, this method is difficult to use as a suitable method for industrially producing orthoalkylated aromatic amines.

It is also proposed in "Friedel Crafts and Related Reactions, Vol. 2, Part 1" by G. A. Olah, published by Interscience Publishers (1964) that aromatic amines such as aniline and the like are reacted with olefins or alcohols in the presence of a Friedel-Crafts type catalyst such as Lewis acids and the like. However, in the case where the amino group of aromatic amines is not substituted, N-alkylated aromatic amines such as N-monoalkyl aromatic amines, N,N-dialkyl aromatic amines or the like are produced as a main product and only a small amount of nucleal-alkylated aromatic amines are formed as by-products. In addition, a mixture of orthoalkylated aromatic amines and paraalkylated aromatic amines is formed as the nucleal-alkylated aromatic amines and the formation ratio of the orthoalkylated aromatic amines is low. This tendency is especially remarkable when an alcohol is used as an alkylating agent. Furthermore, in order to improve the problem of this method, it is proposed in Japanese patent publication No. 38-4569/63 that aromatic amines such as aniline and the like are reacted with olefins under the conditions of a high temperature and a high pressure in the presence of a Friedel-Crafts type catalyst. However, according to this proposed method, although the selectivity to the orthoalkylated aromatic amines somewhat increases, a still large amount of N-alkylated aromatic amines is formed as a by-product and the selective production of the orthoalkylated aromatic amines is difficult. Thus, the conventional processes for producing the orthoalkylated aromatic amines are by no means satisfactory as an industrial process.

Other processes for producing orthoalkylated aromatic amines are as follows. Proposed in U.S. Patent No. 2814646 is a method in which aromatic amines such as aniline and the like are reacted with olefins under heating in the presence of a catalyst comprising aluminum anilide. Proposed in Japanese patent publication No. 47-24014/72 is a method in which aromatic amines such as aniline and the like are reacted with alkylaluminum halide, followed by the reaction of the resultant mixture with olefins. Also proposed in Japanese Patent Laid-Open application No. 50-137934/75 is a method in which aromatic amines such as aniline and the like are reacted with lower olefins in the presence of a catalyst comprising aluminum anilide and halogenated hydrocarbons. Of these methods, the method disclosed in the above-mentioned U.S. Patent No. 2814646 has a disadvantage that the reaction activity is low, although the selectivity to the orthoalkylated aromatic amines in the product is high. On the other hand, methods disclosed in the above-mentioned Japanese Patent Publication No. 47-24014/72 and Japanese Patent Laid-Open Application No. 50-137934/75 have advantages that the reaction activity is high and the selectivity to the orthoalkylated aromatic amines in the product is high. However, since the reactions of these methods should be carried out under a high temperature and high pressure, there is a disadvantage that a reaction apparatus suitable for use in the high temperature and high pressure conditions should be used and, since a substantial amount of the aluminum compound is used as a catalyst. A post treatment operation for removing the aluminum compound from the reaction mixture after the reaction is troublesome. Thus, these methods have many problems from a practical point of view. It should also be noted that, since olefins are used as an alkylating agent in these methods, orthomethylated aromatic amines such as methyl aniline, xylidine and the like or ortho-n-alkylated aromatic amines having a $C_3$ or more alkyl group can not be produced.

It is also known in the prior art, Industrial & Engineering Chemistry 43 [7] 1570–1583(1951), that aniline and methanol are reacted with each other at a vapor phase at a temperature of 360° C. in the presence of various metallic oxide catalysts, whereby N-methyl aniline or N,N-dimethyl aniline is produced. However, it is disclosed in this prior art that silica gel and silica gel with iron oxide were poor catalysts for alkylation.

Accordingly, an object of the present invention is to obviate the above-mentioned problems or disadvantages of the prior arts and to provide a process for selectively producing orthoalkylated aromatic amines on an industrial scale.

Other objects and advantages of the present invention will be apparent from the description set forth herein below.

In accordance with the present invention, there is provided a process for producing an orthoalkylated aromatic amine comprising the step of reacting (a) an aromatic amine having at least one hydrogen atom at the ortho-positions and (b) a primary or secondary alcohol under heating in the presence of a catalyst containing, as a main constituent, iron oxides.

The aromatic amines (a) used as a starting material in the present invention are those which have at least one hydrogen atom at the ortho-positions with respect to the amino or substituted amino group thereof. The aromatic nucleus of the aromatic amines (a) may be a benzene ring, a naphthalene ring, an anthracene ring or a phenanthrene ring. The aromatic amines (a) may be primary aromatic amines, secondary aromatic amines or tertiary aromatic amines. Furthermore, the aromatic amines (a) may have one or more substituents bonded to the carbon atoms of the above-mentioned benzene ring, naphthalene ring, anthracene ring or phenanthrene ring, so long as at least one hydrogen atom is present at the ortho-positions with respect to the amino or substituted amino group. Examples of typical substituents are alkyl groups, aryl groups, alkoxyl groups, aryloxyl groups, acyl groups, acyloxyl groups, halogen atoms, a hydroxyl group and the like.

Typical aromatic amines used as a starting material in the present invention include, for example, aniline, o-toluidine, m-toluidine, p-toluidine, o-ethylaniline, m-ethylaniline, p-ethylaniline, o-isopropylaniline, m-isopropylaniline, p-isopropylaniline, 2,3-xylidine, 2,4-xylidine, 2,5-xylidine, 3,5-xylidine, 2,3-diethylaniline, 2,4-diethylaniline, 2,5-diethylaniline, 3,5-diethylaniline, 2,3-diisopropylaniline, 2,4-diisopropylaniline, 3,5-diisopropylaniline, N-methylaniline, N-ethylaniline, N-isopropylaniline, N,N-dimethylaniline, N,N-diethylaniline, N,N-diisopropylaniline, N-methyl-o-toluidine, N-methyl-2,3-xylidine, N-methyl-2,4-xylidine, N-methyl-2,5-xylidine, N-methyl-3,5-xylidine, N,N-dimethyl-o-toluidine, N,N-dimethyl-m-toluidine, N,N-dimethyl-p-toluidine, N,N-dimethyl-2,3-xylidine, N,N-dimethyl-2,4-xylidine, N,N-dimethyl-2,5-xylidine, N,N-dimethyl-3,5-xylidine, N-ethyl-o-ethylaniline, N-ethyl-m-ethylaniline, N-ethyl-p-ethylaniline, N-ethyl-2,3-diethylaniline, N-ethyl-2,4-diethylaniline, N-ethyl-2,5-diethylaniline, N-ethyl-3,5-diethylaniline, N,N-diethyl-o-ethylaniline, N,N-diethyl-m-ethylaniline, N,N-diethyl-p-ethylaniline, α-naphthylamine, β-naphthylamine and the like. Of these aromatic amines, aniline and o-alkylaniline can be desirably used as a starting material in the present invention.

The alcohols (b) used as a starting material in the present invention are primary or secondary alcohols, generally primary or secondary lower alcohols having 1 to 6 carbon atoms. Typical examples of the primary alcohols are methanol, ethanol, n-propanol, n-butyl alcohol, isobutyl alcohol, n-pentyl alcohol, isopentyl alcohol, n-hexyl alcohol, isohexyl alcohol and the like. Typical examples of the secondary alcohols are isopropanol, sec-butyl alcohol, sec-pentyl alcohol, sec-hexyl alcohol, cyclohexyl alcohol and the like.

Of the above-mentioned alcohols, the use of alcohols having 1 to 3 carbon atoms, especially methanol, ethanol or isopropanol is desirable. Although the amount of the alcohols (b) to be reacted with the above-mentioned aromatic amines may be varied over a wide range, it is generally within the range of from about 1 to about 10 mol, more desirably 3 to 6 mol, based on 1 mol of the aromatic amines.

The catalysts used in the reaction of the present invention are those containing, as a main constituent, iron oxides. The catalysts containing, as a main constituent, iron oxides include catalysts consisting essentially of iron oxides, catalysts comprising iron oxides supported on various carriers, catalysts comprising iron oxides molded by using various binders and the like. The catalysts used in the reaction of the present invention may contain, as a minor constituent, one or more metallic oxides other than the iron oxides in the form of metallic oxide composition. However, it should be noted that the atomic ratio of the iron oxide to the other components contained in the metallic oxide composition, in terms of the metallic element, should be 50:50 or more, preferably 70:30 or more and, more preferably, 90:10 or more. Furthermore, the iron oxides can be in any form of $Fe_2O_3$, $Fe_3O_4$ or any mixtures thereof. The metallic oxides, other than the iron oxide, incorporated into the metallic oxide compositions, as a minor constituent, include, for example: the oxides of typical metallic elements such as aluminum oxide, gallium oxide, silicon oxide, germanium oxide, tin oxide, bismuth oxide, magnesium oxide and the like; and the oxides of transition metallic elements such as copper oxide, titanium oxide, zirconium oxide, hafnium oxide, vanadium oxide, niobium oxide, chromium oxide, molybdenum oxide, tungsten oxide, rhenium oxide and the like. In the case where two or more component type catalysts containing one or more of the above-mentioned components are used in the process of the present invention, the selectivity to the orthoalkylated aromatic amines becomes high and the decomposition of the alcohol in the course of the reaction can be effectively prevented. Especially when a small amount (e.g. 0.5:100 through 10:100, in terms of the atomic ratio of a metallic element of a tertiary component to the iron contained in the iron oxide composition) of the above-mentioned metallic oxide is incorporated, as a tertiary component, into an iron oxide-chromium oxide catalyst or an iron oxide-magnesium oxide catalyst, the resultant three component type catalysts, such as, a Fe-Ge-Cr or Fe-Si-Cr type catalyst, have a desirable long catalyst life time, in addition to the above-mentioned advantages.

The catalysts used in the process of the present invention can be prepared by, for example, the calcination of iron compounds capable of forming iron oxides, the calcination of a mixture comprising iron compounds capable of forming iron oxides and metallic compounds, other than iron compounds, capable of forming metallic oxides which are to be the above-mentioned minor component, or evaporating an aqueous solution of said mixture to dryness, followed by the calcination.

In the case where the catalysts comprising the metallic oxides containing, as a main constituent, the iron oxides supported on carriers, which are used in the process of the present invention, are prepared, iron compounds capable of forming iron oxides by calcination, or if desired, a mixture thereof with metallic compounds, other than the iron compounds, capable of forming metallic oxides which are to be the above-mentioned minor component, are first compounded into carriers and, then, the compounded carriers are molded and calcined. Alternatively, an aqueous solution of the mixture comprising the above-mentioned metallic compounds including the iron compounds is first impregnated into carriers and, then, the resultant carriers are calcined.

According to the present invention, orthoalkylated aromatic amines can be selectively formed by reacting (a) an aromatic amine having at least one hydrogen atom at the ortho-positions and (b) a primary or secondary alcohol under heating in the presence of a catalyst containing, as a main constituent, iron oxides. Although the present reaction can be carried out either in a liquid phase reaction or in a vapor phase reaction, the use of the vapor phase reaction is desirable.

In the case where the present reaction is carried out in a vapor phase reaction, the reaction is carried out at a temperature of generally 200° through 500° C., preferably 250° through 450° C. The liquid space velocity (LHSV) of the starting materials to be fed during the reaction is generally 0.05 through 10 $hr^{-1}$, preferably 0.1 through 2.0 $hr^{-1}$. Although the reaction can be generally carried out under a reduced pressure or under pressure, the reaction is preferably carried out under a pressure of 1 through 30 $kg/cm^2$-G. After the completion of the reaction, the unreacted alcohol is separated from the reaction mixture and, after recovering the unreacted starting aromatic amines, the desired orthoalkylated aromatic amines can be obtained by any conventional treatment, such as, distillation, crystallization, extraction or the like. The recovered unreacted alcohol and aromatic amines having at least one hydrogen atom at the ortho-positions can be reused by circurating the same to the reaction system. The present reaction can be continuously or batchwise carried out.

EXAMPLES

The present invention is now illustrated by, but is by no means limited to, the following examples in which all percentages are expressed on a weight basis unless otherwise specified.

EXAMPLE 1

202.0 g of ferric nitrate.9 hydrates was dissolved in 2 liters of distilled water and, then, a 25% aqueous ammonia was gradually added to the resultant solution, whereby the pH of the solution became 7. The resultant precipitates were washed with water and filtrated. To the filtrated precipitates, 0.55 g of germanium dioxide was added and the resultant mixture was mixed for one hour by using an automatic mill. The mixture was dried at a temperature of 90° C. for about 20 hours and, then, the mixture was calcined at a temperature of 450° C. for 3 hours. Thus, a catalyst comprising iron oxides and germanium oxide was prepared.

20 ml of the crushed catalyst having a size of 6 through 10 meshes (Tyler No.) was packed into a reaction tube made of pyrex and having an inner diameter of 20 mm and, then, heated to a temperature of 370° C. After the temperature reached at the desired level, a liquid mixture having a mol ratio of aniline: methanol = 1:5 was fed at a rate of 14 ml/hr, whereby the reaction was effected. The results are shown in Table 1 below.

EXAMPLE 2

The reaction was carried out in the same manner as in Example 1, except that a liquid mixture having a mol ratio of aniline:methanol:$H_2O$ = 1:5:2 was used as starting materials. The results thus obtained are shown in Table 1 below.

EXAMPLE 3

The reaction was carried out in the same manner as in Example 1, except that the methanol contained in the starting material was changed to ethanol. The results thus obtained are shown in Table 1 below.

COMPARATIVE EXAMPLE 1

The reaction was carried out in the same manner as in Example 1, except that a commercially available silica.alumina catalyst ($SiO_2$:$Al_2O_3$ = 85:15, weight ratio) was used in lieu of the iron oxide catalyst. The results thus obtained are shown in Table 1 below.

EXAMPLE 4

The reaction was carried out in the same manner as in Example 1, except that $Fe_2O_3$ was used as a catalyst. The results thus obtained are shown in Table 1 below.

EXAMPLE 5

The reaction was carried out in the same manner as in Example 1, except that $Fe_2O_3$—$SiO_2$(97/3) was used as a catalyst. The results thus obtained are shown in Table 1 below.

EXAMPLE 6

The reaction was carried out in the same manner as in Example 1, except that $Fe_2O_3$—$GeO_2$—$Cr_2O_3$(96/3/1) was used as a catalyst. The results thus obtained are shown in Table 1 below.

EXAMPLE 7

The reaction was carried out in the same manner as in Example 1, except that $Fe_2O_3$—$GeO_2$(96/4) was used as a catalyst and a liquid mixture of aniline: isopropanol: $H_2O$ having a mol ratio of 1:10:2 was used as a starting material. The results thus obtained are shown in Table 1 below.

EXAMPLE 8

The reaction was carried out in the same manner as in Example 1, except that $Fe_2O_3$—$SiO_2$—$Cr_2O_3$(95/4/1) was used as a catalyst. The results thus obtained are shown in Table 1 below.

EXAMPLE 9

The reaction was carried out in the same manner as in Example 1, except that $Fe_2O_3$—$GeO_2$(70/30) was used as a catalyst. The results thus obtained are shown in Table 1 below.

EXAMPLE 10

The reaction was carried out in the same manner as in Example 1, except that $Fe_2O_3$—$SiO_2$(50/50) was used as a catalyst. The results thus obtained are shown in Table 1 below.

TABLE 1

| | Example 1 | Example 2 | Example 3 | Comparative Example 1 | Example 4 | Example 5 | Example 6 |
|---|---|---|---|---|---|---|---|
| Catalyst (Atomic Ratio of Metals) | $Fe_2O_3$—$GeO_2$ (99/1) | $Fe_2O_3$—$GeO_2$ (99/1) | $Fe_2O_3$—$GeO_2$ (99/1) | $SiO_2$—$Al_2O_3$ (83/17) | $Fe_2O_3$ (100/0) | $Fe_2O_3$—$SiO_2$ (97/3) | $Fe_2O_3$—$GeO_2$—$Cr_2O_3$ (96/3/1) |
| Aniline Conversion (%) | 84.1 | 71.2 | 46.2 | 92 | 32 | 43 | 57 |
| Selectivity (%) to Desired Product* | | | | | | | |
| 2,6-Dialkylaniline | 44.8 | 51.6 | 37.0 | 0.6 | 4.5 | 13 | 43 |
| o-Alkylaniline | 42.2 | 40.2 | 49.2 | 1.3 | 69 | 74 | 54 |
| p-Alkylaniline | 0.4 | 1.2 | 1.2 | 18 | 0.1 | trace | 0.2 |
| N—Alkylaniline | 8.5 | 5.2 | 8.4 | 72.6 | 25 | 8.5 | 0.6 |

TABLE 1-continued

| | | | | | | | |
|---|---|---|---|---|---|---|---|
| N,N—Dialkylaniline | 2.1 | 0.6 | 2.6 | 4.0 | 0.7 | 1.6 | 1.4 |
| o-Alkylation Selectivity (%) | 87.0 | 91.8 | 86.2 | 1.9 | 73.5 | 87 | 97 |

| | | Example 7 | Example 8 | Example 9 | Example 10 |
|---|---|---|---|---|---|
| | Catalyst (Atomic Ratio of Metals) | $Fe_2O_3$—$GeO_2$ (96/4) | $Fe_2O_3$—$SiO_2$—$Cr_2O_3$ (95/4/1) | $Fe_2O_3$—$GeO_2$ (70/30) | $Fe_2O_3$—$SiO_2$ (50/50) |
| | Aniline Conversion (%) | 47.5 | 50.5 | 59 | 85 |
| | Selectivity (%) to Desired Product* | | | | |
| | 2,6-Dialkylaniline | 35.1 | 39 | 34.1 | 32.1 |
| | o-Alkylaniline | 60.2 | 50.1 | 45.3 | 38.2 |
| | p-Alkylaniline | trace | 0.2 | 0.2 | 1.7 |
| | N—Alkylaniline | 3.1 | 8.4 | 20.4 | 17.5 |
| | N,N—Dialkylaniline | trace | 0.5 | 6.4 | 7.4 |
| | o-Alkylation Selectivity (%) | 95.3 | 89.1 | 79.4 | 70.3 |

*Alkyl group:
Examples 1, 2, 4–6 and 8, Comparative Example 1 . . . Methyl group
Example 3 . . . Ethyl group
Example 7 . . . Isopropyl group

We claim:

1. A process for producing an orthoalkylated aromatic amine comprising the step of reacting (a) an aromatic amine having at least one hydrogen atom at the ortho-positions and (b) a primary or secondary alcohol under heating in the presence of a catalyst containing, as a main constituent, iron oxides.

2. A process as claimed in claim 1, wherein said aromatic amine (a) is aniline or o-methylaniline.

3. A process as claimed in claim 1, wherein said alcohol (b) is methanol, ethanol or isopropanol.

4. A process as claimed in claim 1, 2 or 3, wherein the reaction is carried out in a vapor phase reaction.

5. A process as claimed in claim 1, 2 or 3, wherein the reaction is carried out at a temperature of 250° through 450° C.

6. A process as claimed in claim 1, 2 or 3, wherein the amount of the alcohol (b) is 1 through 10 mol, based on 1 mol of the aromatic amine (a).

7. A process as claimed in claim 1, 2 or 3, wherein the catalyst contains 50% by weight or more of the iron oxides, based on the weight of metallic oxide composition contained in the catalyst.

* * * * *